(12) United States Patent
Wang et al.

(10) Patent No.: US 10,835,196 B2
(45) Date of Patent: Nov. 17, 2020

(54) METHOD AND SYSTEMS FOR CAMERA-AIDED X-RAY IMAGING

(71) Applicant: General Electric Company, Schenectady, NY (US)

(72) Inventors: Dejun Wang, Beijing (CN); Srikrishnan V, Bangalore (IN); Gireesha Rao, Pewaukee, WI (US); Katelyn Rose Nye, Milwaukee, WI (US); Nasir Ahmed Desai, Bangalore (IN); Arun Kumar Chandrashekarappa, Bangalore (IN); Huanzhong Li, Beijing (CN)

(73) Assignee: General Electric Company, Schenectady, NY (US)

( * ) Notice: Subject to any disclaimer, the term of this patent is extended or adjusted under 35 U.S.C. 154(b) by 36 days.

(21) Appl. No.: 16/256,843

(22) Filed: Jan. 24, 2019

(65) Prior Publication Data

US 2020/0237332 A1 Jul. 30, 2020

(51) Int. Cl.
*A61B 6/00* (2006.01)
*G06T 7/00* (2017.01)
*H04N 5/32* (2006.01)
*G01T 1/20* (2006.01)

(52) U.S. Cl.
CPC .......... *A61B 6/5241* (2013.01); *A61B 6/542* (2013.01); *G06T 7/0012* (2013.01); *H04N 5/32* (2013.01); *G01T 1/20* (2013.01); *G06T 2207/10116* (2013.01)

(58) Field of Classification Search
CPC ...... A61B 6/544; A61B 6/5441; A61B 6/5241
See application file for complete search history.

(56) References Cited

U.S. PATENT DOCUMENTS

| | | | |
|---|---|---|---|
| 4,613,983 A | 9/1986 | Yedid et al. | |
| 6,463,121 B1 | 10/2002 | Milnes | |
| 6,795,524 B2 | 9/2004 | Hayashi | |
| 6,895,076 B2 | 5/2005 | Halsmer et al. | |
| 6,944,265 B2 | 9/2005 | Warp et al. | |
| 7,177,455 B2 | 2/2007 | Warp et al. | |
| 2004/0114717 A1 | 6/2004 | Kato | |
| 2008/0101538 A1* | 5/2008 | Schliermann | A61B 6/08 378/95 |
| 2010/0020931 A1* | 1/2010 | Otto | A61N 5/1038 378/65 |
| 2010/0290707 A1 | 11/2010 | Wang et al. | |
| 2013/0343523 A1* | 12/2013 | Lee | A61B 6/545 378/63 |

* cited by examiner

*Primary Examiner* — Yara B Green

(57) ABSTRACT

Various methods and systems are provided for x-ray imaging. In one embodiment, a method for an image pasting examination comprises acquiring, via an optical camera and/or depth camera, image data of a subject, controlling an x-ray source and an x-ray detector according to the image data to acquire a plurality of x-ray images of the subject, and stitching the plurality of x-ray images into a single x-ray image. In this way, optimal exposure techniques may be used for individual acquisitions in an image pasting examination such that the optimal dose is utilized, stitching quality is improved, and registration failures are avoided.

17 Claims, 5 Drawing Sheets

METHOD AND SYSTEMS FOR CAMERA-AIDED X-RAY IMAGING

FIELD

Embodiments of the subject matter disclosed herein relate to x-ray imaging.

BACKGROUND

Image pasting, or the creation of a composite image, is usually accomplished by having a system for acquiring images with a total field-of-view larger than the detector field-of-view (FOV). For applications such as full-spine imaging or long-legs imaging, the total coverage of anatomy (e.g., 60-120 cm) exceeds that of most current detectors and film-screen systems. In one approach to overcome the limitations of the detector FOV, multiple images are acquired during an image pasting exam with overlapping FOVs and stitched together. Historically, images were acquired with the detector FOV, and the various images are then cut manually by a radiologist to avoid overlaps and repasted manually to reconstruct an image with the total FOV. More recently, automatic techniques for digitally pasting successive images have increased the accuracy of image pasting exams.

BRIEF DESCRIPTION

In one embodiment, a method for an image pasting examination comprises acquiring, via an optical camera, image data of a subject, controlling an x-ray source and an x-ray detector according to the image data to acquire a plurality of x-ray images of the subject, and stitching the plurality of x-ray images into a single x-ray image. In this way, optimal exposure techniques may be used for individual acquisitions in an image pasting examination such that the optimal dose is utilized, stitching quality is improved, and registration failures are avoided.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 2:
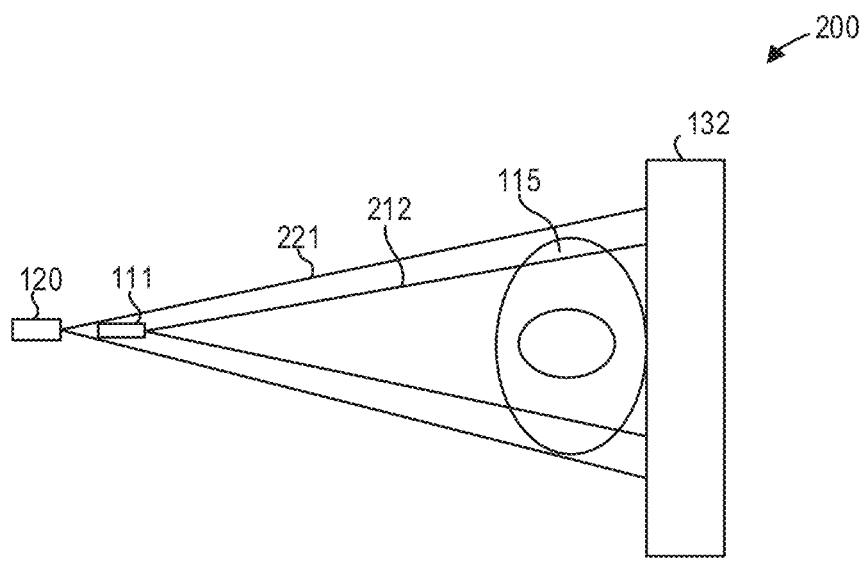
FIG. 2 shows a diagram illustrating the field of view for a camera and an x-ray source relative to a patient according to an embodiment.
Figure 3:
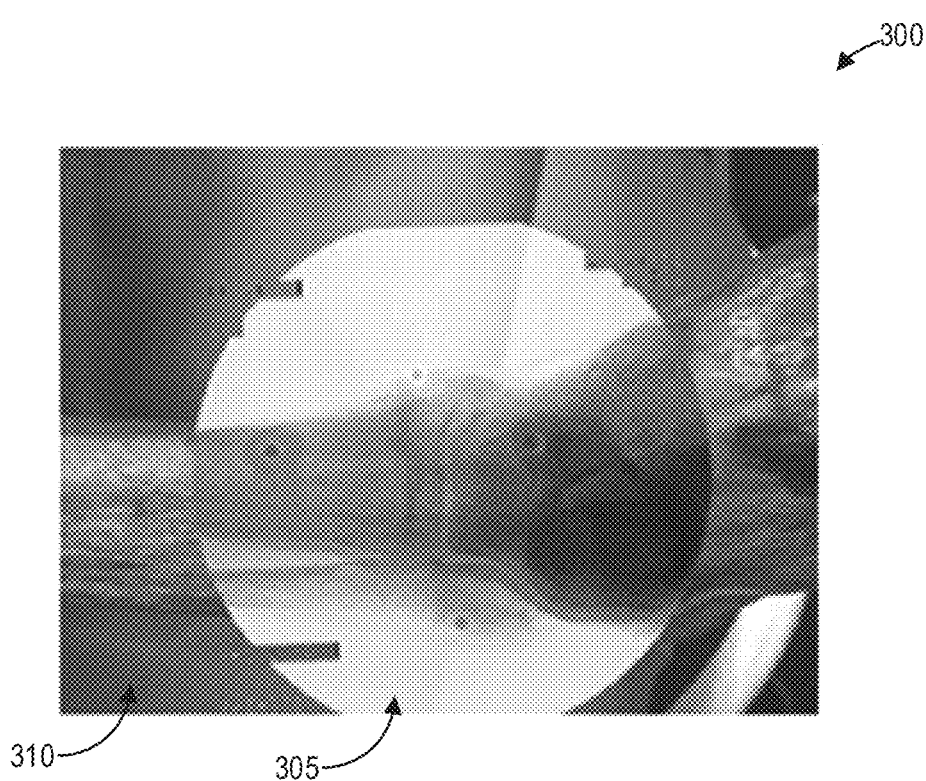
FIG. 3 shows an image illustrating an example overlay of camera images and x-ray images according to an embodiment.
Figure 4:
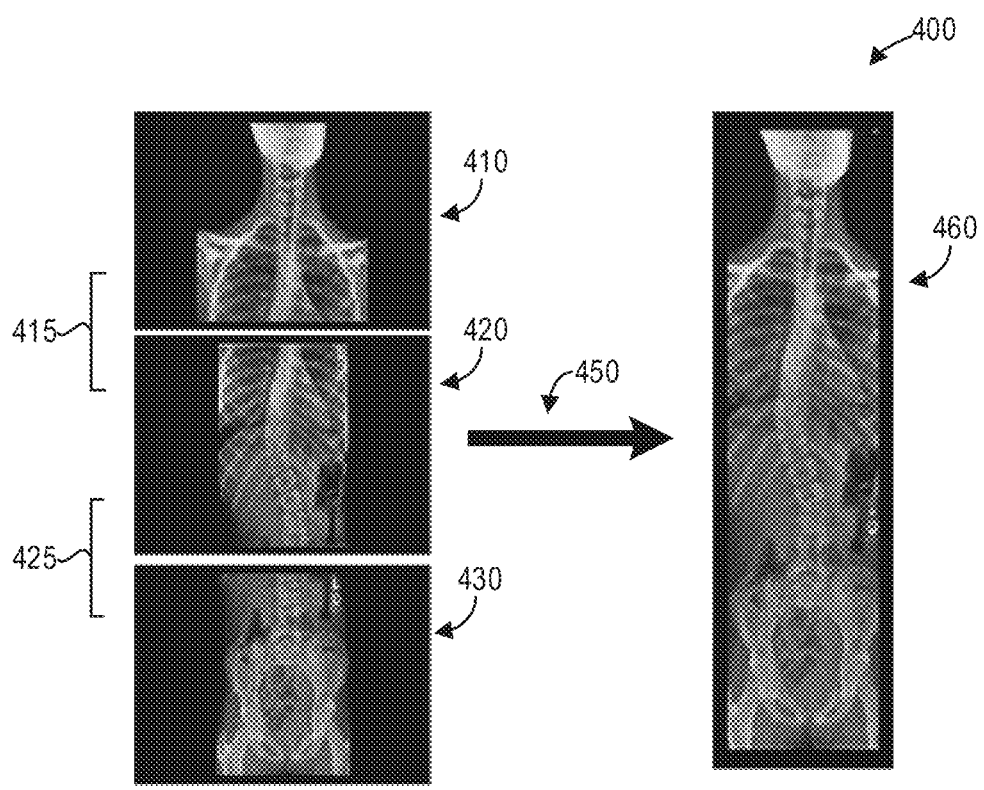
FIG. 4 shows a diagram illustrating an example stitching of multiple x-ray images into a single x-ray image according to an embodiment.

The following description relates to various embodiments of x-ray imaging. In particular, systems and methods for camera-aided x-ray imaging are provided. An x-ray imaging system, such as the x-ray imaging system depicted in FIG. 1, includes an optical depth camera positioned adjacent to and co-calibrated with an x-ray source. The field-of-view of the camera may overlap the field-of-view of the x-ray source, as depicted in FIGS. 2 and 3. During an image pasting exam, multiple images may be acquired and pasted into a single image, as depicted in FIG. 4. The images should be registered because perceptible anatomical mismatches are present at the given resolution despite calibration of the tilting mechanism for acquiring the separate images. However, registration of the images suffers from poor accuracy if there is insufficient or poor contrast or image pre-processing fails in the overlapped field-of-view. A method for ensuring consistent image contrast while also optimizing the radiation dose, such as the method depicted in FIG. 5, includes estimating patient thickness from image data from the camera to determine optimal exposure parameters. Further, a method for an image pasting exam, such as the method depicted in FIG. 6, includes acquiring both optical images and x-ray images with the camera and x-ray source, respectively, accurately registering the optical images, and stitching the x-ray images according to the registration of the optical images.

Figure 1:
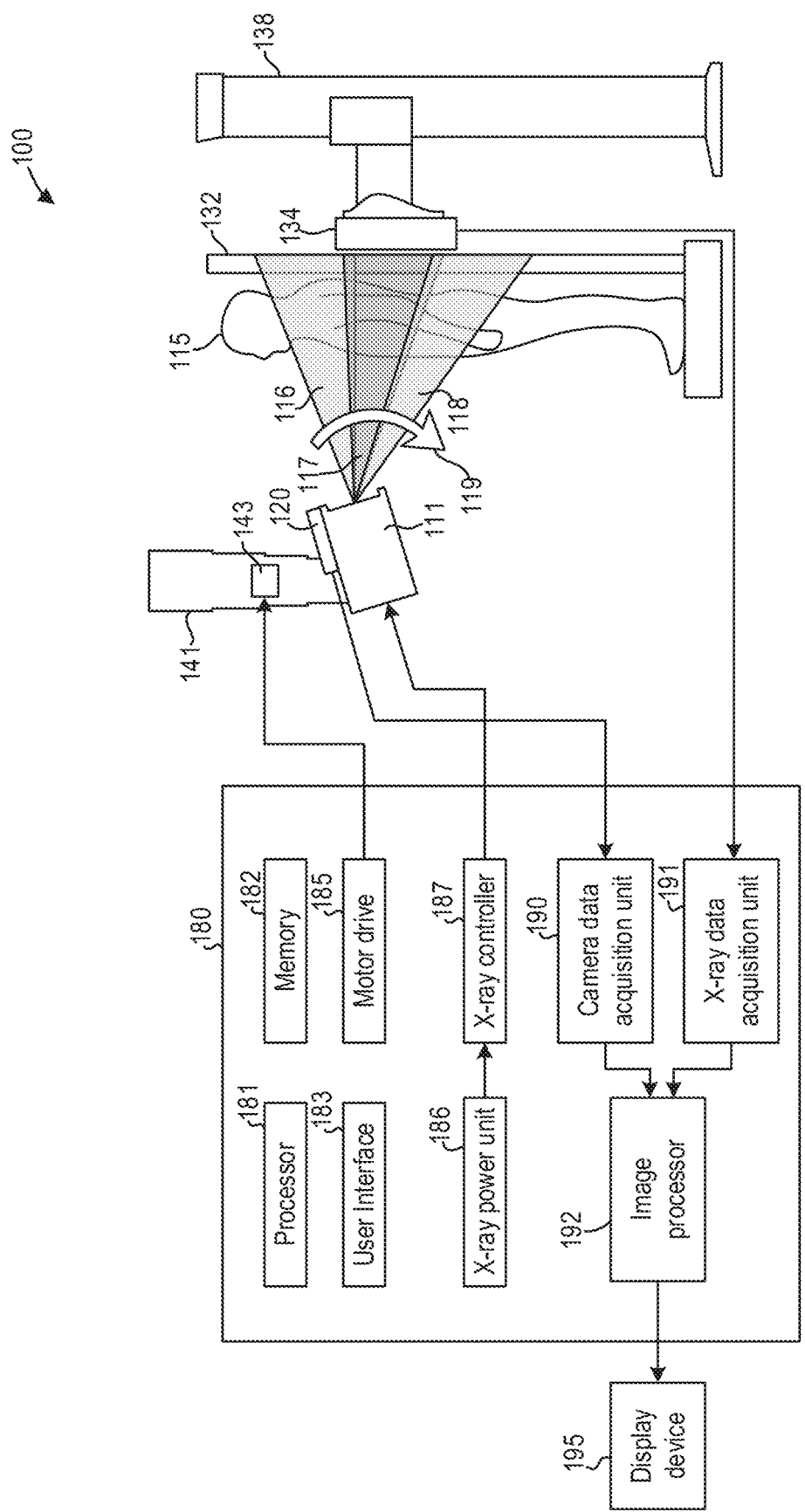
FIG. 1 shows an example x-ray imaging system according to an embodiment.

Turning now to FIG. 1, a block diagram of an x-ray imaging system 100 in accordance with an embodiment is shown. The x-ray imaging system 100 includes an x-ray source 111 which radiates x-rays, a stand 132 upon which the subject 115 stands during an examination, and an x-ray detector 134 for detecting x-rays radiated by the x-ray source 111 and attenuated by the subject 115. The x-ray detector 134 may comprise, as non-limiting examples, a scintillator, one or more ion chamber(s), a light detector array, an x-ray exposure monitor, an electric substrate, and so on. The x-ray detector 134 is mounted on a stand 138 and is configured so as to be vertically moveable according to an imaged region of the subject.

The operation console 180 comprises a processor 181, a memory 182, a user interface 183, a motor drive 185 for controlling one or more motors 143, an x-ray power unit 186, an x-ray controller 187, a camera data acquisition unit 190, an x-ray data acquisition unit 191, and an image processor 192. X-ray image data transmitted from the x-ray detector 134 is received by the x-ray data acquisition unit 191. The collected x-ray image data are image-processed by the image processor 192. A display device 195 communicatively coupled to the operating console 180 displays an image-processed x-ray image thereon.

The x-ray source 111 is supported by a support post 141 which may be mounted to a ceiling (e.g., as depicted) or mounted on a moveable stand for positioning within an imaging room. The x-ray source 111 is vertically moveable relative to the subject or patient 115. For example, one of the one or more motors 143 may be integrated into the support post 141 and may be configured to adjust a vertical position of the x-ray source 111 by increasing or decreasing the distance of the x-ray source 111 from the ceiling or floor, for example. To that end, the motor drive 185 of the operation console 180 may be communicatively coupled to the one or more motors 143 and configured to control the one or more motors 143.

The x-ray power unit 184 and the x-ray controller 182 supply power of a suitable voltage current to the x-ray source 111. A collimator (not shown) may be fixed to the x-ray source 111 for designating an irradiated field-of-view of an x-ray beam. The x-ray beam radiated from the x-ray source 111 is applied onto the subject via the collimator.

A camera 120 may be positioned adjacent to the x-ray source 111 and may be co-calibrated with the x-ray source 111. The camera 120 may comprise an optical camera that detects electromagnetic radiation in the optical range. Additionally or alternatively, the camera 120 may comprise a depth camera or range imaging camera. As an illustrative and non-limiting example, the camera 120 configured as a depth camera may include an optical camera, an infrared camera, and an infrared projector which projects infrared dots in the field-of-view of the camera 120. The infrared camera images the dots, which in turn may be used to measure depth within the optical camera of the camera 120. As another illustrative and non-limiting example, the camera 120 may comprise a time-of-flight camera. The camera 120 is communicatively coupled to the camera data acquisition unit 190 of the operation console 180. Camera data acquired or generated by the camera 120 may thus be transmitted to the camera data acquisition unit 190, which in turn provides acquired camera image data to the image processor 192 for image processing. For example, as described further herein, the image processor 192 may process the acquired camera images to identify a position of a desired anatomical region for imaging and/or to measure or estimate the thickness of the subject 115 at the desired anatomical region. Further, in some examples, the image processor 192 may stitch and register camera images to determine stitching and registration parameters for the x-ray images.

The field-of-view of the camera 120 may overlap the field-of-view of the x-ray source 111. For example, FIG. 2 shows a diagram 200 illustrating the field-of-view 221 for the camera 120 and the field-of-view 212 of the x-ray source 111 relative to the subject 115. As depicted, the field-of-view 221 of the camera 120 overlaps the field-of-view 212 of the x-ray source 111 relative to the subject 115. As an additional illustrative example, FIG. 3 shows an image illustrating an example overlay 300 of a camera image 310 and an x-ray image 305 according to an embodiment. Thus, as depicted in FIGS. 2 and 3, the field-of-view of the camera 120 overlaps and is aligned with the field-of-view of the x-ray source 111 relative to the subject 115.

Referring again to FIG. 1, the x-ray source 111 and the camera 120 may pivot or rotate relative to the support post 141 in an angular direction 119 to image different portions of the subject 115. For example, during an image pasting examination, multiple x-ray images of the subject 115 may be acquired at different angles and pasted or stitched together to form a single image. As depicted, the x-ray source 111 may be oriented with a first field-of-view 116 to acquire a first x-ray image. The x-ray source 111 may then be rotated in the angular direction 119 to a second field-of-view 117 to acquire a second x-ray image. The x-ray source 111 may then be rotated in the angular direction 119 to a third field-of-view 118 to acquire a third x-ray image. The three fields-of-view 116, 117, and 118 are depicted as partially overlapping. The three x-ray images acquired may thus be stitched together as described further herein to form a single x-ray image.

FIG. 4 shows a diagram 400 illustrating an example stitching of multiple x-ray images into a single x-ray image according to an embodiment. In particular, a first x-ray image 410 and a second x-ray image 420 may be acquired with the first field-of-view 116 and the second field-of-view 117, respectively, with an overlapping region 415 between the first x-ray image 410 and the second x-ray image 420. A third x-ray image 430 may also be acquired with the third field-of-view 118, with an overlapping region 425 between the second x-ray image 420 and the third x-ray image 430. The three x-ray images may then be image pasted or stitched 450 into a single x-ray image 460.

Patient thickness varies from patient to patient, exam to exam, and throughout the body parts of a single patient. This variation makes it difficult to pre-set or manually set acquisition exposure parameters for individual exposures of an image pasting exam. Poor exposure techniques result in stitching failures, poor image quality from under- or over-exposure, excessive radiation exposure of a patient, or inability to complete the exam due to a generator failure.

The camera 120 of the x-ray imaging system 100 enables the determination of optimal exposure techniques for the x-ray source 111. For example, the image processor 192 may process camera image data from the camera 120 to accurately estimate the thickness of anatomical regions for each acquisition. According to the thickness for each acquisition, optimal exposure settings may be determined, for example from a look-up table (not shown) stored in the memory 182, for each acquisition. By optimizing the exposure settings prior to the x-ray acquisition, the optimal balance may be achieved between x-ray penetration and contrast.

Furthermore, prior x-ray imaging systems rely on the correct positioning of desired anatomical regions to be stitched over the location of the ion chambers of the x-ray detector, which are in fixed locations relative to the detector area. Patients with scoliosis, for example, may have part of the spine over the ion chamber in one stitched image but not another, resulting in over- or under-exposure of the various stitched images. This may be avoided by leveraging the camera sensor outputs of the camera 120 to match the appropriate ion chambers of the x-ray detector 134 to the anatomical regions for each stitched image.

Figure 5:
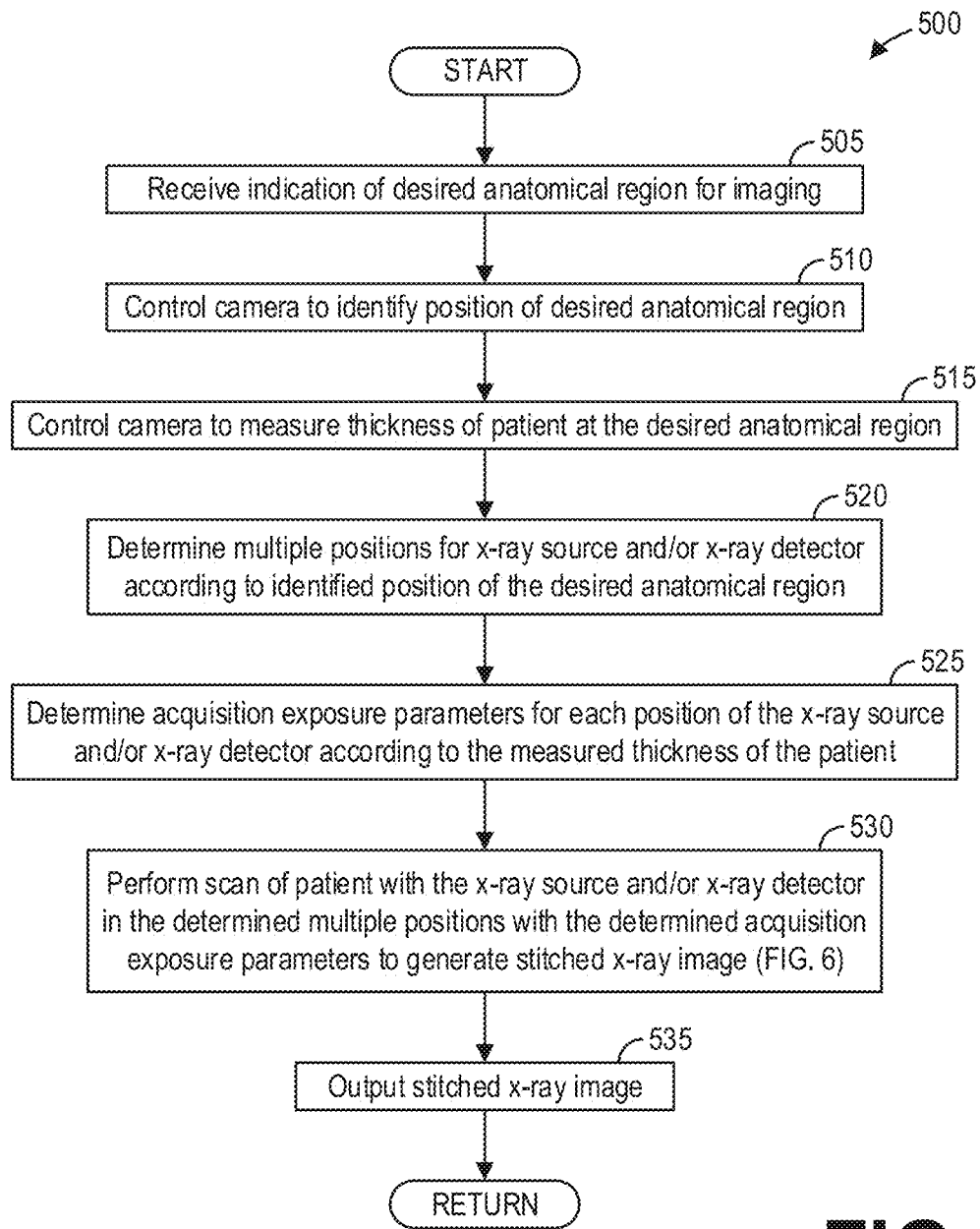
FIG. 5 shows a high-level flow chart illustrating an example method for optimizing x-ray exposure parameters and x-ray detector positions according to an embodiment.

FIG. 5 shows a high-level flow chart illustrating an example method 500 for optimizing x-ray exposure parameters and x-ray detector positions according to an embodiment. In particular, method 500 relates to using images or image data from an optical camera to optimize control of an x-ray source and/or x-ray detector during an image pasting examination. Method 500 is described with regard to the systems and components of FIG. 1, though it should be appreciated that the method 500 may be implemented with other systems and components without departing from the scope of the present disclosure. Method 500 may be stored as executable instructions in non-transitory memory, such as memory 182, and may be executed by a processor, such as processor 181, of the x-ray imaging system 100.

Method 500 begins at 505. At 505, method 500 receives an indication of a desired anatomical region for imaging. For example, an operator of the x-ray imaging system 100 may input or select, via the user interface 183, a desired anatomical region of a subject for imaging. The desired anatomical region may comprise, as non-limiting examples, the entire spine of the subject, a particular portion of the spine of the subject, legs of the subject, and so on. At 510, method 500 controls the camera to identify the position of the desired anatomical region. For example, method 500 may generate control signals to drive one or more motors 143 via the motor drive 185 to adjust a position of the camera 120. Camera data or images generated by the camera 120 may be received via the camera data acquisition unit 190, for example, as the position of the camera 120 relative to the subject 115 is adjusted via the one or more motors 143. The image processor 192 may process the images to automatically identify the position of the desired anatomical region of the subject 115.

Further, at 515, method 500 controls the camera to measure the thickness of the patient at the desired anatomical region. For example, the thickness of the subject 115 at the desired anatomical region may be estimated from the images acquired via the camera 120 while identifying the position of the desired anatomical region. As another example, the camera 120 may comprise a depth camera or a range imaging camera configured to measure the distance of points in a two-dimensional image from the camera 120. In this way, the thickness of the subject 115 at the desired anatomical region may be more accurately measured, as the depth of the subject 115 may be directly measured via the camera 120.

Continuing at 520, method 500 determines multiple positions for the x-ray source and/or the x-ray detector according to the identified position of the desired anatomical region. For example, method 500 may determine a plurality of angular positions or vertical positions of the x-ray source 111 such that the field-of-view of the x-ray source 111 across the plurality of angular or vertical positions covers the desired anatomical region. Furthermore, method 500 may determine a vertical position of the x-ray detector 134 that corresponds with the angular or vertical position of the x-ray source 111 for a given position of the x-ray source. For example, as depicted in FIG. 1, the x-ray detector 134 may be moved upwards or downwards vertically to match the first field-of-view 116 of the x-ray source 111, the second field-of-view 117 of the x-ray source 111, and the third field-of-view 118 of the x-ray source 111. Method 500 may thus determine such vertical positions for the x-ray detector 134 to ensure that ion chambers of the x-ray detector 134, for example, are correctly positioned to detect x-rays emitted by the x-ray source 111 and passing through the desired anatomical region of the subject 115.

At 525, method 500 determines acquisition exposure parameters for each position of the x-ray source and/or x-ray detector according to the measured thickness of the patient. For example, optimized exposure parameters may be predetermined for various anatomical regions and thicknesses and stored in one or more look-up tables. In such an example, method 500 may select exposure parameters from the one or more look-up tables according to the measured thickness of the subject 115. Further, the exposure parameters may vary for different positions of the x-ray source, as the thickness of the corresponding anatomical region of the subject may vary. In this way, uneven x-ray penetration due to patient thickness variations may be avoided, thereby improving stitching quality, reducing registration failures, and reducing unnecessary x-ray dose.

At 530, method 500 performs a scan of the patient with the x-ray source and/or x-ray detector in the determined multiple positions with the determined acquisition exposure parameters to generate a stitched x-ray image. To that end, method 500 may control the one or more motors 143 to adjust the positions of the x-ray source 111 and/or the x-ray detector 134 relative to the subject 115, and furthermore method 500 may control the x-ray source 111 with the corresponding exposure parameters to optimally image the desired anatomical region of the subject 115. A plurality of x-ray images may thus be acquired during the scan and stitched into a single x-ray image.

Furthermore, in some examples, the camera 120 may acquire images during the scan which may be leveraged for stitching the x-ray images. Such a method for scanning the patient is described further herein with regard to FIG. 6.

At 535, method 500 outputs the stitched x-ray image. Method 500 may output the stitched x-ray image, for example to a display device 195 for display. The displayed x-ray image may depict the desired anatomical region, wherein the span of the desired anatomical region is greater than the field-of-view of the x-ray source 111. Further, due to the tailoring of the exposure parameters for the specific subject 115, the displayed x-ray image may appear as a single x-ray image without apparent discontinuities between the individual x-ray images comprising the displayed x-ray image. Method 500 then returns.

Figure 6:
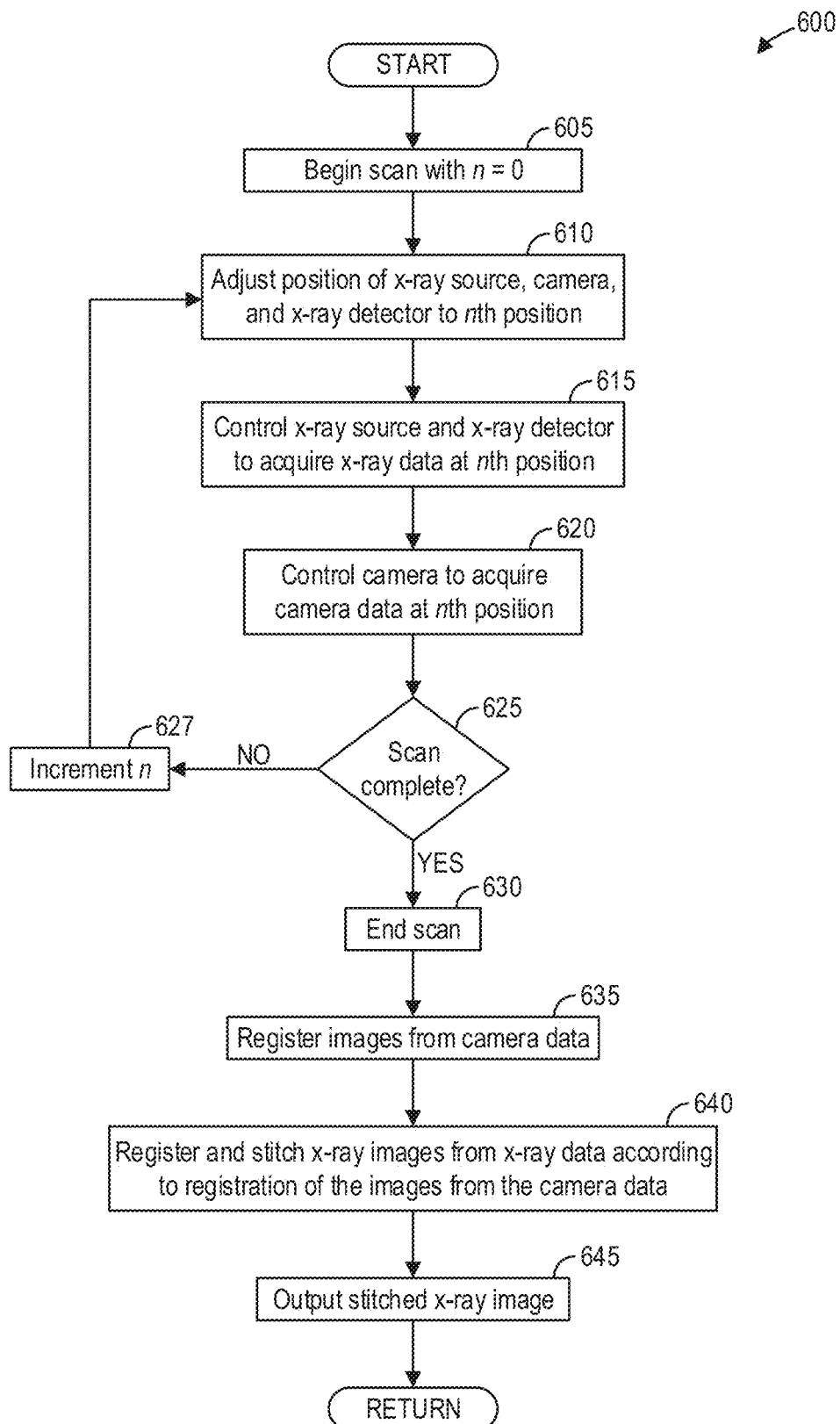
FIG. 6 shows a high-level flow chart illustrating an example method for generating an x-ray image from multiple x-ray images acquired at different positions according to an embodiment.

FIG. 6 shows a high-level flow chart illustrating an example method 600 for generating an x-ray image from multiple x-ray images acquired at different positions according to an embodiment. In particular, method 600 relates to controlling an x-ray source and an optical camera to acquire x-ray images and optical images during a scan, and stitching the x-ray images into a single x-ray image based on the optical images. Method 600 is described with regard to the systems and components of FIG. 1, though it should be appreciated that the method 600 may be implemented with other systems and components without departing from the scope of the present disclosure. Method 600 may be stored as executable instructions in non-transitory memory, such as memory 182, and may be executed by a processor, such as processor 181, of the x-ray imaging system 100.

Method 600 begins at 605. At 605, method 600 begins a scan with an iteration number n equal to zero. At 610, method 600 adjusts the position of the x-ray source, the camera, and the x-ray detector to the nth position. For example, method 600 may control the one or more motors 143 via the motor drive 185 to adjust the positions of the x-ray source 111, the camera 120, and/or the x-ray detector 134. During the first iteration of the scan wherein n=0, the nth position comprises a zeroth position or initial position of the x-ray source 111, the camera 120, and the x-ray detector 134. As an illustrative example, the zeroth position of the x-ray source 111 may be the angular position such that the field-of-view of the x-ray source 111 comprises the first field-of-view 116 depicted in FIG. 1. The corresponding field-of-view of the camera 120, which may be positioned adjacent to the x-ray source 111 and may be moveable with the x-ray source 111 to the zeroth position, may be configured to align with and overlap the field-of-view of the x-ray source 111, as depicted in FIGS. 2 and 3. The zeroth position of the x-ray detector 134 may correspond to the zeroth position of the x-ray source 111 such that x-rays emitted from the x-ray source 111 in the zeroth position impinge upon the x-ray detector 134.

At 615, method 600 controls the x-ray source and the x-ray detector to acquire x-ray image data at the nth position. In particular, method 600 may control the x-ray source 111 according to the determined acquisition exposure parameters for the nth position as determined by method 500. Continuing at 620, method 600 controls the camera to acquire camera data at the nth position. At 625, method 600 determines if the scan is complete. The scan is complete when the iteration number n equals N, or the total number of positions.

If the scan is not complete ("NO"), method 600 continues to 627, where method 600 increments the iteration number n by one. Method 600 then returns to 610 to acquire data at the next position. For example, when n=1, method 600 adjusts the position of the x-ray source 111, the camera 120, and/or the x-ray detector 134 to the first position and acquires x-ray data and camera data at the first position. As an illustrative example, the x-ray source 111 in the first position may have the second field-of-view 117 depicted in FIG. 1. As noted in FIG. 1, the second field-of-view 117 may at least partially overlap the first field-of-view 116 imaged in the zeroth position. After acquiring x-ray data and camera data in the first position, method 600 may increment n by one such that n=2 at 627 and return to 610. Method 600 then adjusts the position of the x-ray source 111, the camera 120, and/or the x-ray detector 134 to a second position and acquire x-ray data and camera data at the second position. As an illustrative example, the x-ray source 111 in the second position may have the third field-of-view 118 depicted in FIG. 1, which at least partially overlaps the second field-of-view 117 imaged in the first position. Method 600 thus iteratively images the subject with different overlapping fields-of-view until the iteration number n equals the total number of positions N.

Once the iteration number n equals the total number of positions N, the scan is complete ("YES"). Method 600 then continues to 630, where method 600 ends the scan. Continuing at 635, method 600 registers the images from the camera data. That is, method 600 registers the images acquired at 620 across the iterations. The registration of the camera images is performed in a pairwise manner. The registration method may comprise any suitable method such as sum-of-squares minimization, entropy-based metrics like cross-correlation, and so on. As one example, a formulation of registration includes:

$$E^{RGB}(T;I_1^{RGB},I_2^{RGB})=\int S[I_1^{RGB}(x),I_2^{RGB}(T(x))]dx$$

where the energy function E is minimized and the transform parameters $$T=[t_x,t_y,t_\theta]$$

are obtained, typically in an iterative fashion. At 640, method 600 registers and stitches the x-ray images from the x-ray data according to the registration of the images from the camera data. For example, a similar equation for registering the x-ray images as above may be used to register the x-ray images, with the transform parameters T obtained for the camera images used as an initialization for the transform parameters of the x-ray image registration. The cost function for the x-ray image registration may be modified.

As another example of performing registration, a combined cost function account for both the camera images $I^{RGB}$ and the x-ray images $I^X$ may be utilized:

$$E(T;I_1^{RGB},I_2^{RGB},I_1^X,I_2^X)=(1.0-\lambda)E^{RGB}(T;I_1^{RGB},I_2^{RGB})+\lambda E^X(T;I_1^X,I_2^X)$$

wherein the weight $\lambda$ ranges from 0 to 1 and controls the importance of RGB and x-ray image registration. Initially the parameter $\lambda$ would be low and is decreased as registration progresses iteratively.

Finally, after registering and stitching the x-ray images into a single x-ray image, method 600 continues to 645. At 645, method 600 outputs the stitched x-ray image. Method 600 may output the stitched x-ray image, for example, to a display device 195 for display. Further, method 600 may output the stitched x-ray image to storage, such as memory 182, for subsequent retrieval and review. In some examples, method 600 may output the stitched x-ray image, the optical images, and/or the registration parameters may be stored in non-transitory memory, such as memory 182, for subsequent retrieval. For example, during a subsequent examination of the patient, one or more of the prior optical images, stitched images, registration parameters, or image-paste angle and range (i.e., the n positions for acquiring images in the imaging range) may be accessed by the system 100 and used for determining parameters for the subsequent examination. In this way, the system 100 may know a priori what angle or range should be used, for example, to capture a particular anatomy of interest such as a metal stem implant, which may be in the leg and the entire leg should be imaged as the radiologist likely wants to evaluate the entire implant. After outputting at least the stitched x-ray image, method 600 then returns.

A technical effect of the disclosure includes the optimization of x-ray exposure for multiple acquisitions according to thickness or depth of a subject being imaged, wherein the exposure and the thickness varies across the multiple acquisitions. Another technical effect of the disclosure is the display of an x-ray image of an anatomical region that spans a distance greater than the field-of-view of an x-ray source. Yet another technical effect of the disclosure includes the accurate positioning of an x-ray detector and an x-ray source relative to a desired anatomical region for imaging.

In one embodiment, a method for an image pasting examination comprises acquiring, via an optical camera, image data of a subject, controlling an x-ray source and an x-ray detector according to the image data to acquire a plurality of x-ray images of the subject, and stitching the plurality of x-ray images into a single x-ray image.

In a first example of the method, the method further comprises determining, from the image data, exposure parameters for the x-ray source for a plurality of angular positions of the x-ray source. In a second example of the method optionally including the first example, controlling the x-ray source according to the image data comprises controlling the x-ray source with the exposure parameters to generate an x-ray beam at each angular position of the plurality of angular positions. In a third example of the method optionally including one or more of the first and second examples, the method further comprises determining, from the image data, one or more positions for an x-ray detector for each angular position of the plurality of angular positions of the x-ray source. In a fourth example of the method optionally including one or more of the first through third examples, the method further comprises adjusting a position of the x-ray detector to the one or more positions for each angular position of the x-ray source to acquire the plurality of x-ray images. In a fifth example of the method optionally including one or more of the first through fourth examples, a field-of-view of the x-ray source covers a different portion of the subject for the plurality of angular positions of the x-ray source, and determining, from the image data, exposure parameters for the x-ray source for the plurality of angular positions of the x-ray source comprises measuring, from the image data, a thickness of the subject at the different portions for the plurality of angular positions, and selecting exposure parameters for each angular position according to the thickness of the subject. In a sixth example of the method optionally including one or more of the first through fifth examples, the image data comprises images of the subject acquired at a plurality of angular positions relative to the subject, further comprising registering the images of the subject. In a seventh example of the method optionally including one or more of the first through sixth examples, the method further comprises stitching the plurality of x-ray images into the single x-ray image according to the registration of the images. In an eighth example of the method optionally including one or more of the first through seventh examples, registering the images of the subject comprises iteratively minimizing a cost function with the images input to the cost function to obtain transform parameters, and wherein stitching the plurality of x-ray images into the single x-ray image according to the registration of the images comprises registering the plurality of x-ray images with the transform parameters.

In another embodiment, a method comprises acquiring image data of the subject via a camera prior to a scan of a subject, controlling an x-ray source according to the image data to generate a plurality of x-ray images during the scan, and stitching the plurality of x-ray images into a single x-ray image according to image data acquired via the camera during the scan.

In a first example of the method, acquiring the image data via the camera prior to the scan comprises controlling the camera to identify a position of a desired anatomical region of the subject for imaging. In a second example of the method optionally including the first example, the method further comprises measuring a thickness of the subject at the desired anatomical region from the image data, determining a plurality of x-ray source positions for the x-ray source according to the position of the desired anatomical region, and determining exposure parameters for the x-ray source at the plurality of x-ray source positions according to the thickness of the subject at the desired anatomical region. In a third example of the method optionally including one or more of the first and second examples, controlling the x-ray source according to the image data to generate the plurality of x-ray images comprises controlling the x-ray source with the exposure parameters to generate x-rays at the plurality of x-ray source positions, and detecting the generated x-rays with an x-ray detector to generate the plurality of x-ray images. In a fourth example of the method optionally including one or more of the first through third examples, the camera comprises a depth camera, and measuring the thickness of the subject at the desired anatomical region from the image data comprises measuring the depth of the subject at the desired anatomical region with the camera.

In yet another embodiment, an x-ray imaging system comprises an x-ray source for generating x-rays, an optical camera positioned adjacent to the x-ray source, an x-ray detector configured to detect the x-rays, and a processor configured with instructions in non-transitory memory that when executed cause the processor to: acquire, via the optical camera, image data of a subject; control the x-ray source and the x-ray detector according to the image data to acquire a plurality of x-ray images of the subject; and stitch the plurality of x-ray images into a single x-ray image.

In a first example of the system, the system further comprises one or more motors, wherein the processor is further configured with instructions that when executed cause the processor to control the one or more motors to adjust a position of the x-ray source relative to the subject to acquire the plurality of x-ray images. In a second example of the system optionally including the first example, the processor is further configured with instructions that when executed cause the processor to estimate a thickness of the subject, and determine exposure parameters for the x-ray source according to the thickness, wherein controlling the x-ray source according to the image data to acquire the plurality of x-ray images comprises controlling the x-ray source with the determined exposure parameters. In a third example of the system optionally including one or more of the first and second examples, the optical camera comprises a depth camera, and wherein the processor estimates the thickness of the subject based on depths of the subject measured via the optical camera. In a fourth example of the system optionally including one or more of the first through third examples, the processor is further configured with instructions in non-transitory memory that when executed cause the processor to register a plurality of images acquired via the optical camera, and stitch the plurality of x-ray images into the single x-ray image according to the registration of the plurality of images. In a fifth example of the system optionally including one or more of the first through fourth examples, the system further comprises a display device, wherein the processor is further configured with instructions in the non-transitory memory that when executed cause the processor to output the single x-ray image to the display device for display.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for an image pasting examination, comprising:
    acquiring, via an optical camera, image data of a subject;
    controlling an x-ray source and an x-ray detector according to the image data to acquire a plurality of x-ray images of the subject;
    stitching the plurality of x-ray images into a single x-ray image;
    wherein the image data comprises optical images of the subject acquired at a plurality of angular positions relative to the subject, further comprising registering the optical images of the subject; and
    stitching the plurality of x-ray images into the single x-ray image according to the registration of the optical images.

2. The method of claim 1, further comprising determining, from the image data, exposure parameters for the x-ray source for a plurality of angular positions of the x-ray source.

3. The method of claim 2, wherein controlling the x-ray source according to the image data comprises controlling the x-ray source with the exposure parameters to generate an x-ray beam at each angular position of the plurality of angular positions.

4. The method of claim 2, further comprising determining, from the image data, one or more positions for an x-ray detector for each angular position of the plurality of angular positions of the x-ray source.

5. The method of claim 4, further comprising adjusting a position of the x-ray detector to the one or more positions for each angular position of the x-ray source to acquire the plurality of x-ray images.

6. The method of claim 2, wherein a field-of-view of the x-ray source covers a different portion of the subject for the plurality of angular positions of the x-ray source, and wherein determining, from the image data, exposure parameters for the x-ray source for the plurality of angular positions of the x-ray source comprises measuring, from the image data, a thickness of the subject at the different portions for the plurality of angular positions, and selecting exposure parameters for each angular position according to the thickness of the subject.

7. The method of claim 1, wherein registering the optical images of the subject comprises iteratively minimizing a cost function with the optical images input to the cost function to obtain transform parameters, and wherein stitching the plurality of x-ray images into the single x-ray image according to the registration of the optical images comprises registering the plurality of x-ray images with the transform parameters.

8. A method, comprising:
prior to a scan of a subject, acquiring image data of the subject via a camera;
during the scan, controlling an x-ray source according to the image data to generate a plurality of x-ray images; and
stitching the plurality of x-ray images into a single x-ray image according to image data acquired via the camera during the scan;
register a plurality of camera images acquired via the camera, and stitch the plurality of x-ray images into the single x-ray image according to the registration of the plurality of camera images.

9. The method of claim 8, wherein acquiring the image data via the camera prior to the scan comprises controlling the camera to identify a position of a desired anatomical region of the subject for imaging.

10. The method of claim 9, further comprising measuring a thickness of the subject at the desired anatomical region from the image data, determining a plurality of x-ray source positions for the x-ray source according to the position of the desired anatomical region, and determining exposure parameters for the x-ray source at the plurality of x-ray source positions according to the thickness of the subject at the desired anatomical region.

11. The method of claim 10, wherein controlling the x-ray source according to the image data to generate the plurality of x-ray images comprises controlling the x-ray source with the exposure parameters to generate x-rays at the plurality of x-ray source positions, and detecting the generated x-rays with an x-ray detector to generate the plurality of x-ray images.

12. The method of claim 10, wherein the camera comprises a depth camera, and wherein measuring the thickness of the subject at the desired anatomical region from the image data comprises measuring the depth of the subject at the desired anatomical region with the camera.

13. An x-ray imaging system, comprising:
an x-ray source for generating x-rays;
an optical camera positioned adjacent to the x-ray source;
an x-ray detector configured to detect the x-rays; and
a processor configured with instructions in non-transitory memory that when executed cause the processor to:
acquire, via the optical camera, image data of a subject;
control the x-ray source and the x-ray detector according to the image data to acquire a plurality of x-ray images of the subject;
stitch the plurality of x-ray images into a single x-ray image;
register a plurality of images acquired via the optical camera, and stitch the plurality of x-ray images into the single x-ray image according to the registration of the plurality of images.

14. The system of claim 13, further comprising one or more motors, wherein the processor is further configured with instructions that when executed cause the processor to control the one or more motors to adjust a position of the x-ray source relative to the subject to acquire the plurality of x-ray images.

15. The system of claim 13, wherein the processor is further configured with instructions that when executed cause the processor to estimate a thickness of the subject, and determine exposure parameters for the x-ray source according to the thickness, wherein controlling the x-ray source according to the image data to acquire the plurality of x-ray images comprises controlling the x-ray source with the determined exposure parameters.

16. The system of claim 15, wherein the optical camera comprises a depth camera, and wherein the processor estimates the thickness of the subject based on depths of the subject measured via the optical camera.

17. The system of claim 13, further comprising a display device, wherein the processor is further configured with instructions in the non-transitory memory that when executed cause the processor to output the single x-ray image to the display device for display.

* * * * *